United States Patent [19]
Nisonoff

[11] Patent Number: 6,103,257
[45] Date of Patent: Aug. 15, 2000

[54] SYSTEM FOR DELIVERING PHARMACEUTICALS TO THE BUCCAL MUCOSA

[75] Inventor: Keith Nisonoff, Highlands Ranch, Colo.

[73] Assignee: Num-Pop, Inc., Denver, Colo.

[21] Appl. No.: 09/118,485

[22] Filed: Jul. 17, 1998

[51] Int. Cl.⁷ .......................... A61K 9/00; A61K 31/245
[52] U.S. Cl. .......................... 424/440; 514/536; 514/817
[58] Field of Search .......................... 424/440; 514/535, 514/536, 537, 817, 818

[56] References Cited

U.S. PATENT DOCUMENTS

| | | | |
|---|---|---|---|
| 4,139,627 | 2/1979 | Lane et al. | 424/267 |
| 4,367,738 | 1/1983 | Legendre et al. | 604/110 |
| 4,372,942 | 2/1983 | Cimiluca | 424/440 |
| 4,551,329 | 11/1985 | Harris et al. | 424/22 |
| 4,599,354 | 7/1986 | Shulman | 514/530 |
| 4,647,459 | 3/1987 | Peters et al. | 424/155 |
| 4,671,953 | 6/1987 | Stanley et al. | 424/440 |
| 4,761,274 | 8/1988 | Denick, Jr. et al. | 424/48 |
| 4,855,326 | 8/1989 | Fuisz | 514/777 |
| 4,863,737 | 9/1989 | Stanley et al. | 424/440 |
| 4,917,894 | 4/1990 | Matthias et al. | 424/440 |
| 4,971,798 | 11/1990 | Coia et al. | 424/440 |
| 5,055,461 | 10/1991 | Kelleher et al. | 514/162 |
| 5,064,651 | 11/1991 | Mochizuki et al. | 424/440 |
| 5,085,634 | 2/1992 | Lackney | 604/77 |
| 5,122,127 | 6/1992 | Stanley | 604/890.1 |
| 5,132,114 | 7/1992 | Stanley et al. | 424/440 |
| 5,223,259 | 6/1993 | Lackney | 424/435 |
| 5,240,704 | 8/1993 | Tsurumizu et al. | 424/85.8 |
| 5,288,497 | 2/1994 | Stanley et al. | 424/440 |
| 5,484,602 | 1/1996 | Stanley et al. | 424/440 |
| 5,520,924 | 5/1996 | Chapman et al. | 424/435 |
| 5,567,733 | 10/1996 | Dishler | 514/567 |
| 5,614,207 | 3/1997 | Shah et al. | 424/440 |
| 5,747,060 | 5/1998 | Sackler et al. | 424/426 |

OTHER PUBLICATIONS

The Merck Index, 8th ed. Rahway: Merck & Co., Inc. pp. 431, 451, 676, 1023, 1968.

*Primary Examiner*—Jeffrey E. Russel
*Attorney, Agent, or Firm*—LeBoeuf, Lamb, Greene, MacRae L.L.P.; John R. Posthumus, Esq.

[57] ABSTRACT

The present invention is a system which topically delivers pharmaceuticals to the buccal mucosa. Preferred pharmaceuticals include topical local anesthetics, such as tetracaine, which can be applied to the mucosa for rapid pain relief. The system comprises a hard candy matrix in which the pharmaceutical is dispersed. The hard candy matrix may be formed without the addition of dyes, synthetic flavoring agents, alcohols, or preservatives. Also, the candy may be mounted on a handle to form a lollipop, and the handle may be used to position the candy adjacent a particular site where the pharmaceutical is needed.

19 Claims, 1 Drawing Sheet

6,103,257

SYSTEM FOR DELIVERING PHARMACEUTICALS TO THE BUCCAL MUCOSA

FIELD OF THE INVENTION

The present invention relates generally to delivery systems for pharmaceuticals, and more specifically to a composition and method for topically administering local anesthetics to the oral and pharyngeal mucosa. The composition and method are particularly suitable for administering a topical anesthetic, such as tetracaine, to small children for relieving pain caused by irritation of the oral and pharyngeal mucosa.

BACKGROUND OF THE INVENTION

Sore throats, sores, and other irritations in mouth and pharynx are common ailments that can cause pain. Although a variety of pharmaceuticals are available, both prescription and over-the-counter, to treat the pain, these pharmaceuticals can be sometimes difficult to administer to patients who are unwilling and/or unable to take conventional oral medications. For example, children and adults may have difficulty swallowing tablets or capsules. Patients may resist taking medicine in liquid form due to the medicine's unpleasant taste or texture or difficulty in swallowing. Moreover, there may be a significant time delay, sometimes twenty minutes or longer, between ingesting many oral medications and the onset of a therapeutic effect because the medications must be absorbed into the blood stream from the digestive system after the medicine is swallowed.

Lozenges, which may consist of one or more pharmaceuticals into a candy carrier, have been used to deliver medications, either topically within the buccal cavity of the patient or by swallowing the pharmaceutical after it has dissolved in saliva. Generally, each lozenge includes a quantity of one or more pharmaceuticals sufficient to deliver an effective dose to the average patient when the entire lozenge is consumed. However, many patients are affected differently by that dose, with some being more sensitive and some being less sensitive to the effects. Further, lozenges for administering medicine may be inappropriate in some circumstances because there is a chance a patient may choke on the lozenge.

Lollipops have been used to deliver pharmaceuticals to patients. In particular, lollipops containing the potent, short-acting narcotic fentanyl have been approved by the FDA for the treatment of severe pain, such as might be encountered in conjunction with surgical and other medical procedures, from cancer, and from opportunistic infections associated with HIV infection.

SUMMARY OF THE INVENTION

The present invention comprises a system for topical delivery of one or more pharmaceuticals to the buccal mucosa for localized treatment, such as for rapid pain relief. In this regard, it is observed that some pharmaceuticals which are either lipophilic or capable of being rendered lipophilic in the buccal cavity may be administered by lollipops. The lipophilicity of these drugs makes them susceptible to rapid absorption into the blood stream through the mucosa of the mouth. This absorption occurs much more rapidly than when the pharmaceuticals are swallowed and absorbed via the digestive system. Further, because the absorption is rapid, the dose can easily be controlled by administering the lollipop only until the desired effect is observed, thereby minimizing the dose. The pharmaceuticals which are absorbed through the mucosa are transported by the blood stream to remote sites in the body and may have a systemic effect. In accordance with the present invention, the pharmaceutical is incorporated into a hard candy matrix for topical delivery to a selected site within the buccal cavity.

It is therefore an object of the present invention to provide a composition and method for relieving pain due to inflammation of a patient's buccal mucosa.

It is a further object of the present invention to provide a composition and method for topically applying pharmaceuticals to a patient's buccal mucosa, wherein the composition is free of dyes, alcohols, preservatives, and synthetic flavoring agents.

It is a further object of the present invention to provide a method for making compositions suitable for topical application of pharmaceuticals to a patient's buccal mucosa.

One aspect of the present invention includes a medicine for topically anesthetizing a patient's oral and pharyngeal mucosa. In this regard, at least one pharmaceutical selected from injectable local anesthetics is dispersed in a hard candy matrix. The pharmaceutical is present in the hard candy matrix in a quantity sufficient to topically anesthetize the patient's oral or pharyngeal mucosa when at least a portion of the hard candy dissolves in the patient's mouth.

In one embodiment of the present invention, the medicine is provided in the form of a candy matrix in which the pharmaceutical is dispersed. The medicine may also be molded about a handle which is operable to position the medicine adjacent a selected area of the patient's mucosa. The hard candy matrix may be substantially free of allergens and additives such as synthetic flavorings, dyes, preservatives, and alcohols. The pharmaceutical is preferably dispersed in the candy matrix in a quantity sufficient to deliver an effective topical dose of the pharmaceutical to the mucosa when the patient sucks on the medicine for a predetermined time period, which may be about two minutes or less. The quantity of the pharmaceutical in the topical dose may be selected on the basis of the patient's weight and/or the patient's age.

Preferred pharmaceuticals include esters of benzoic acid, para-aminobenzoic acid, meta-aminobenzoic acid, para-ethoxybenzoic acid; amides of benzoic acid and benzoic acid derivatives; and a pharmaceutically acceptable salts thereof. Tetracaine and tetracaine salts are particularly suitable for use in the present invention. The quantity of tetracaine dispersed in the hard candy matrix is preferably between about 700 mg and about 1500 mg per 250 cubic centimeters of hard candy matrix, and, more preferably, between about 800 mg and about 1000 mg per 250 cubic centimeters of hard candy matrix. Most preferably, the dispersed quantity of tetracaine is between about 1100 mg and about 1500 mg per 250 cubic centimeters of hard candy matrix.

Another aspect of the invention includes a medicine for topically applying a pharmaceutical to a patient's oral/pharyngeal mucosa. The medicine comprises a hard candy matrix in which a quantity of the pharmaceutical is dispersed. The quantity of the pharmaceutical is sufficient to provide a pharmaceutically effective dose when the medicine dissolves in the patient's mouth, and the hard candy matrix is substantially free of components selected from synthetic flavorings, synthetic dyes, preservatives, and alcohols. Preferably, the pharmaceutical is substantially non-absorbable into the patient's bloodstream through the mucosa.

Yet another aspect of the invention includes a method for preparing a hard candy composition for topically applying a pharmaceutical to the oral/pharyngeal mucosa of a patient. The method comprises the steps of preparing a molten mixture comprising at least one sugar and water in proportions which will create a hard candy matrix when the mixture is at ambient temperature; dispersing a quantity of the pharmaceutical in the molten mixture; and forming the mixture containing the dispersed pharmaceutical into an object sized for insertion into a patient's mouth and allowing the mixture to cool to form a hard candy. The quantity of the pharmaceutical in the hard candy is sufficient to deliver an effective topical dose of the pharmaceutical to the mucosa of the patient when at least a portion of the object dissolves in the patient's mouth. The pharmaceutical is selected from esters of benzoic acid, para-aminobenzoic acid, meta-aminobenzoic acid, para-ethoxybenzoic acid; amides of benzoic acid and benzoic acid derivatives; and pharmaceutically acceptable salts thereof. The preparing step may further comprise the steps of providing a mixture of sugar and water, and heating the mixture to form a solution having a boiling point selected to ensure that the proportion of sugar to water in the solution is sufficient to create the hard candy. The method may comprise an additional step of mixing at least one ingredient selected from flavoring agents, coloring agents, preservatives, alcohols, and stabilizers into the molten mixture. The method also may comprise an additional step of cooling the molten mixture to a temperature at which the mixture remains molten and the pharmaceutical is stable when dispersed in the mixture. In this regard, the cooling step occurs prior to the dispersing step.

In one embodiment, the pharmaceutical is tetracaine. Preferably, in the dispersing step, the quantity of tetracaine in the hard candy is between about 700 mg and about 1500 mg per 250 cubic centimeters of hard candy. More preferably, the quantity of tetracaine is between about 800 mg and about 1000 mg per 250 cubic centimeters of hard candy. Most preferably, the quantity of tetracaine present in the hard candy object is between about 1100 mg and about 1500 mg per 250 cubic centimeters of hard candy.

Yet another aspect of the present invention includes a method for topically administering a pharmaceutical to the buccal mucosa of a patient. In this regard, the pharmaceutical is selected from the group of esters of benzoic acid, para-aminobenzoic acid, meta-aminobenzoic acid, para-ethoxybenzoic acid; amides of benzoic acid and benzoic acid derivatives; and pharmaceutically acceptable salts thereof. The method comprises the steps of inserting a hard candy object into the patient's mouth, wherein a quantity of the pharmaceutical is dispersed in the hard candy object, and removing the hard candy object from the patient's mouth after a period of time sufficient for at least a portion of the hard candy object to dissolve in the patient's saliva and provide an effective dose of the pharmaceutical to the patient to achieve a desired local effect of the pharmaceutical on the patient's mucosa. The quantity of the pharmaceutical is sufficient to provide the effective dose of the pharmaceutical for localized topical administration of the pharmaceutical to the mucosa when the matrix dissolves in the patient's mouth.

The period of time is preferably between about 30 seconds and about 2 minutes. More preferably, the period is between about 45 seconds and about 90 seconds.

Preferably the pharmaceutical is tetracaine, which is preferably present in a quantity between about 700 mg and about 1500 mg per 250 cubic centimeters of the hard candy object. More preferably, the quantity of tetracaine is between about 800 mg and about 1000 mg per 250 cubic centimeters of the hard candy object. Most preferably, the quantity of the tetracaine is between about 1100 mg and about 1500 mg per 250 cubic centimeters of the hard candy object.

The hard candy object may include a handle for inserting the object into the patient's mouth, positioning the object in the patient's mouth, and removing the object from the patient's mouth, and the method may further comprise the step of using the handle to position the hard candy object in the patient's mouth adjacent a selected portion of the patient's mucosa to deliver the effective dose to the selected portion.

DETAILED DESCRIPTION

Figure 1:
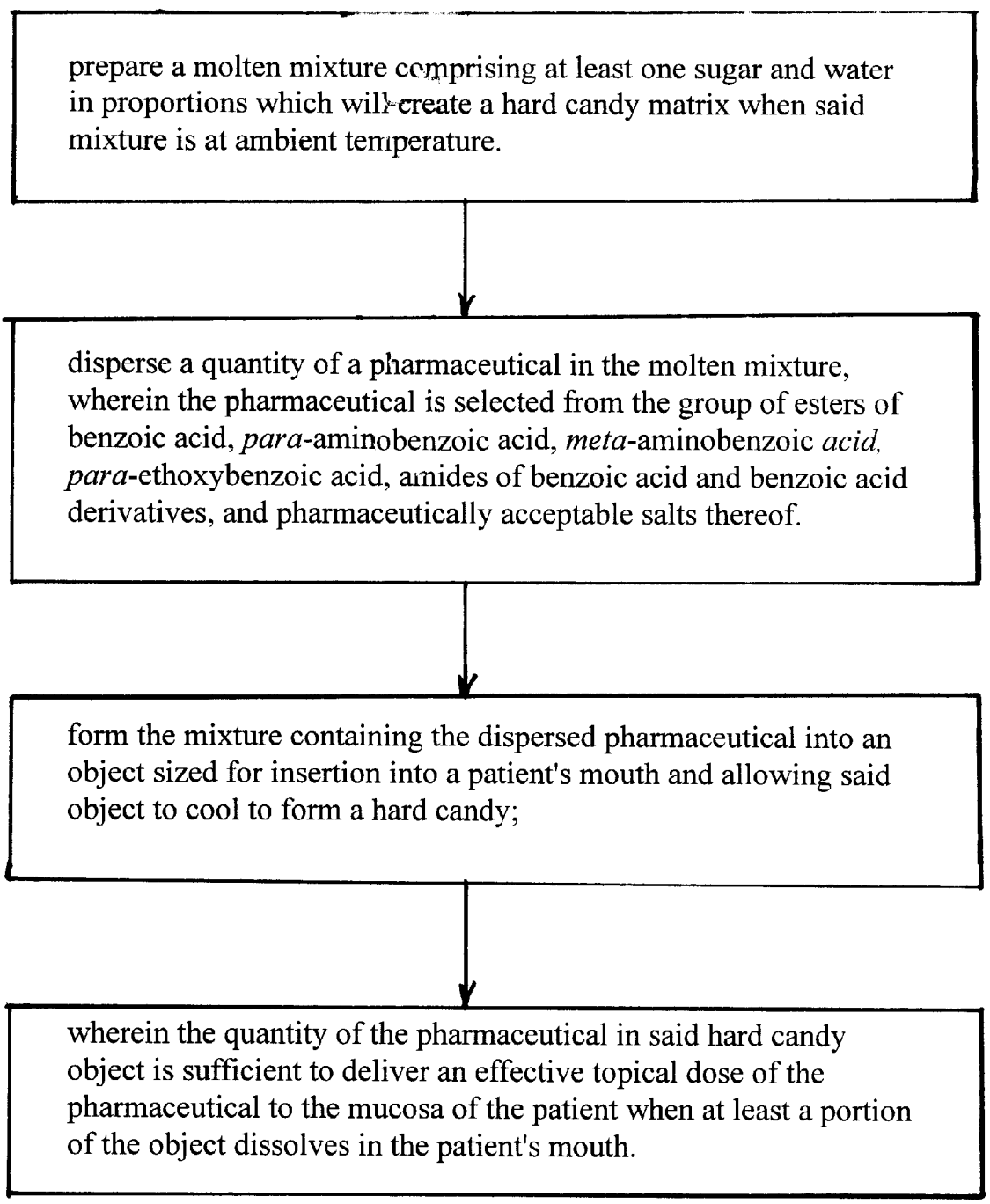
FIG. 1 shows a flow chart describing the steps to make a hard candy medicine in accordance with one aspect of the present invention.

The present invention comprises a novel system for topical delivery of pharmaceuticals to the buccal mucosa, such as for the localized treatment of pain. In accordance with the present invention, a pharmaceutical is incorporated into a hard candy matrix for topical delivery within the buccal cavity. In a preferred embodiment, the hard candy is mounted on a handle to form a lollipop. Thus, the pharmaceutical can be delivered to a specific site, such as to provide rapid, localized pain relief. Because the candy is mounted on a handle, it is suitable for administering the pharmaceutical to small children and to other patients who are unable and/or unwilling to take medicines in liquid, tablet, or capsule form. As used herein, the term "buccal" refers to the mouth and pharynx, and the "buccal mucosa" includes the mucosa of the mouth and pharynx.

Generally referencing FIG. 1, the hard candy matrix of the present invention is formed by heating a mixture of one or more sugars to a temperature high enough to evaporate sufficient water to form a molten mass which can form uniform, small crystals upon cooling. The mass must remain molten at a temperature low enough to allow the pharmaceutical and other ingredients, such as flavoring agents, to be added without degradation.

Suitable pharmaceuticals for use in the present invention are those which can be dispersed or dissolved in a molten candy mixture without being degraded by the relatively high temperature of the melt. Preferably, the pharmaceutical is soluble and stable in a molten mixture of one or more sugars and water. Preferably, the pharmaceutical also is not absorbed significantly through the mucosa and remains at the site where it is applied topically. Even if a portion of the pharmaceutical is absorbed through the mucosa, the systemic dose received when the pharmaceutical is administered as described below would be quite small and probably much less than a dose which could produce a systemic effect. Pharmaceuticals which are not absorbed appreciably through the mucosa tend to be non-lipophilic.

A preferred type of pharmaceutical is a topical local anesthetic. More preferably, the anesthetic is selected from the group of esters of benzoic acid, para-aminobenzoic acid, meta-aminobenzoic acid, para-ethoxybenzoic acid, amides of benzoic acid and benzoic acid derivatives, and pharmaceutically acceptable salts thereof. Many of these anesthetics are injectable topical anesthetics. One suitable anesthetic is tetracaine, the 2-(dimethylamino)ethyl ester of 4-(butylamino) benzoic acid. As used herein, the term "tetracaine" refers to tetracaine and to salts of tetracaine, such as tetracaine hydrochloride (tetracaine HCl). Tetracaine HCl is available in powder form and has, to date, been used primarily for spinal anesthesia, for topical application to the eye, and for dental infiltration. Tetracaine HCl has a melting point of about 148° F. and is very soluble in water. Further, tetracaine HCl is stable in the candy matrix and does not react with the candy or otherwise degrade during long-term storage. It has been found that tetracaine HCl can be incorporated into a candy matrix without the use of preservatives or suspending agents. Tetracaine is a preferred anesthetic also because it acts for a relatively long period of time, and because it is rapidly converted into substantially nontoxic metabolites in the stomach if the patient swallows all or part of the piece of candy. Moreover, the tetracaine remaining in the swallowed candy will have no further effect on the mucosa.

The quantity of tetracaine or another suitable anesthetic should be sufficient to provide local anesthesia adequate to rapidly reduce or eliminate pain due to the inflammation of the mucosa, without totally anesthetizing the area. In other words, the preferred effective dose relieves discomfort but still allows enough sensation for the patient to engage in normal activities, such as speaking, chewing, and swallowing. The effective dose will vary for different patients, depending on a number of factors including the particular individual's age, weight, and sensitivity. The dose can be controlled both by varying the quantity of the anesthetic in the candy matrix and the length of time the patient sucks on the candy. The effects of the local anesthetic can be felt rapidly, often with about one minute. The candy can be prepared such that the anesthetic concentration is suitable for small children or for adults. Because of the rapid action, the anesthetic can be administered as needed for pain, without significant danger of overdosing.

It should be noted that the effective dose of tetracaine administered in accordance with the present invention is considerably less than the tetracaine doses which have previously been used for topical application. Tetracaine HCl is available in the United States as a 2% solution for topical application to tissues. This solution strength is used to provide complete numbing of the tissues to which it is applied. The concentration of tetracaine or tetracaine HCl in the candy in accordance with the present invention is equivalent to a 1% solution, making it about an order of magnitude less, and the tetracaine HCl is even further diluted when the candy dissolves over time in the patient's saliva.

In addition to the anesthetic, various flavoring agents, coloring agents, dispersants, stabilizers, preservatives may be added to the molten candy. However, it has been found that tetracaine HCl can be incorporated into an attractive and palatable candy matrix without the use of any dyes, alcohols, preservatives, or synthetic flavoring agents. The candy matrix can be formulated without chemical additives, making it advantageous to individuals who wish to avoid consuming such additives, and particularly advantageous to individuals who are allergic or otherwise sensitive to additives, such as dyes, preservatives, and synthetic flavoring agents, which are unnecessary for the desired pharmacological effect.

It should be emphasized that the use of a medicated lollipop is advantageous for a number of reasons. Lollipops provide a pleasant way for a reluctant patient to receive the pharmaceutical. Lollipops are suitable for administering the anesthetic to small children because the stick helps prevent accidental swallowing of the entire lollipop, and the stick allows a care giver to easily insert the candy into and remove the candy from a patient's mouth. Also, by mounting the anesthetic-containing candy on a stick, the pharmaceutical can be administered at a specific site of pain, such as a sore in the patient's mouth.

In accordance with the present invention, objects made from the medicated candy can be sucked by a patient until the pain is significantly or completely masked by the anesthetic. If the candy is supplied in the form of a lollipop, the lollipop can be removed from the patient's mouth when the desired anesthetic effect is obtained. The lollipop may then be wrapped to keep it clean and stored for reuse. The lollipop can be reused as needed to control the pain and as often as every 30 minutes.

The invention is further illustrated by the following examples.

EXAMPLE 1

A candy matrix is formed by mixing one cup (240 grams) of sugar, ⅓ cup (81 cc) of light corn syrup, and slightly more than 1 cup (240 ml) of water. The matrix mixture is heated to a temperature of at least 285° F., taking care to avoid stirring the mixture at temperatures greater than 200° F. to prevent uncontrolled crystallization of the sugar mixture. The matrix mixture is allowed to cool to 260° F., and 4 ml of a flavoring agent and ⅛ teaspoon (0.625 cc) of citric acid are added, followed by the addition of 900 mg of tetracaine HCl. These ingredients are stirred thoroughly into the matrix, and the resulting mixture is poured into molds which have been sprayed with an anti-stick coating, such as for example the anti-stick coating known under the trademark PAM. The sticks are inserted 2 minutes after pouring into the molds. It should be noted that the mixture contains no die, no alcohol, no synthetic flavor agents and no preservatives, and is completely natural.

EXAMPLE 2

A molten candy matrix is prepared by combining 1 cup (240 grams) of sugar, ⅓ cup (81 cc) of light corn syrup, and ¼ cup (60 ml) of water. The sugars and the water are mixed well and heated to 300° F. The mixture is not stirred after the temperature reaches 200° F. The matrix mixture is removed from the heat, and 1.35 g of tetracaine and 1 ml of natural tangerine oil are stirred into the matrix mixture. The resulting mixture is cooled to about 260° F. and poured into molds. The sticks are inserted into the candy within a few minutes of being poured, and the lollipops are allowed to cool completely. The cooled medicated candy is pale yellow and tangerine flavored. It should be noted that the mixture contains no die, no alcohol, no synthetic flavor agents, and no preservatives, and is completely natural.

EXAMPLE 3

Medicated lollipops are prepared as described in Example 2, except that 900 mg of tetracaine and ⅛ teaspoon (0.625 cc) of citric acid are added to the hot candy matrix mixture. It was discovered that the citric acid caused the hardened candy to have an orange color.

EXAMPLE 4

Medicated lollipops are prepared as described in Example 2. An adult, with a severe canker sore in his mouth, places one of the lollipops in his mouth adjacent the sore for about 90 seconds. The site of the sore becomes numb and pain-free for about 30 minutes. The lollipop is wrapped and stored for reuse. The treatment is repeated as needed, at intervals of at least 30 minutes, until the sore heals and the pain subsides.

EXAMPLE 5

Medicated lollipops are prepared as described in Example 3. A three-year-old girl who has been diagnosed with strep throat is given one of the lollipops to suck, and instructed to keep her head back to allow saliva in which the tetracaine is dissolved to contact her throat. After about one minute, the lollipop is removed from the girl's mouth, and she immediately says her throat doesn't hurt. The treatment is repeated as needed to control the sore throat pain at intervals of at least 30 minutes until the inflammation due to the infection is gone.

EXAMPLE 6

Medicated lollipops are prepared as described in Example 2 and stored in a refrigerator for six months. Even without the addition of any preservatives or stabilizers, the lollipops have approximately the same potency as when they were made, indicating that the tetracaine is substantially stable in the candy.

While specific embodiments of this invention have been disclosed, it is expected that killed in the art can and will design alternate embodiments of this invention that fall the scope of the appended claims.

What is claimed is:

1. A medicine for topically anesthetizing a patient's buccal mucosa, said medicine comprising:
    a handle;
    a hard candy matrix; and
    tetracaine,
    wherein said tetracaine is dispersed in said hard candy matrix in a quantity sufficient to topically anesthetize the patient's oral or pharyngeal mucosa when at least a portion of said hard candy dissolves in the patient's mouth;
    wherein said hard candy matrix is substantially free of synthetic flavorings, synthetic dyes, preservatives, and alcohols;
    wherein said hard candy matrix and said dispersed tetracaine are molded about said handle;
    wherein said handle is operable to position said hard candy matrix and said dispersed tetracaine adjacent a selected area of said mucosa;
    wherein said tetracaine is dispersed in said candy matrix in a quantity sufficient to deliver an effective topical dose of said tetracaine to said mucosa when the patient sucks on said hard candy matrix and said dispersed tetracaine for a time period.

2. The medicine of claim 1, wherein said time period is no more than about two minutes.

3. The medicine of claim 1, wherein said quantity of said tetracaine in said hard candy matrix is determined on the basis of at least one parameter selected from the group consisting of the patient's weight and the patient's age.

4. A medicine for topical anesthesia of a patient's buccal mucosa, said medicine comprising:
    a hard candy matrix; and
    tetracaine dispersed in said hard candy matrix;
    wherein said tetracaine provides a pharmaceutically effective dose when said medicine dissolves in the patient's mouth;
    wherein said hard candy matrix is substantially free of synthetic flavorings, synthetic dyes, preservatives, and alcohols.

5. The medicine of claim 4, wherein said dispersed tetracaine is present in a quantity between about 700 mg and about 1500 mg per 250 cubic centimeters of said hard candy matrix.

6. The medicine of claim 4, wherein said dispersed tetracaine is present in a quantity between about 800 mg and about 1000 mg per 250 cubic centimeters of said hard candy matrix.

7. The medicine of claim 4, wherein said dispersed tetracaine is present in a quantity between about 1100 mg and about 1500 mg per 250 cubic centimeters of said hard candy matrix.

8. A method for preparing a hard candy medicine for topically applying a pharmaceutical to the buccal mucosa of a patient, said method comprising the steps of:
    preparing a molten mixture consisting of at least one sugar and water in proportions which will create a hard candy matrix when said mixture is at ambient temperature;
    heating said molten mixture;
    dispersing a quantity of tetracaine in said heated molten mixture;
    forming said mixture containing said dispersed tetracaine into an object sized for insertion into a patient's mouth and allowing said object to cool to form a hard candy;
    wherein said quantity of said tetracaine in said hard candy object is sufficient to deliver an effective topical dose of said tetracaine to the mucosa of the patient when at least a portion of said object dissolves in the patient's mouth.

9. The method of claim 8, further comprising the step of:
    mixing at least one ingredient selected from the group consisting of flavoring agents, coloring agents, preservatives, alcohols, and stabilizers into said molten mixture.

10. The method of claim 8, wherein said dispersing step includes dispersing a quantity of tetracaine so as to result in a concentration of between about 700 mg and about 1500 mg per 250 cubic centimeters in said hard candy object.

11. The method of claim 8, wherein said dispersing step includes dispersing a quantity of tetracaine so as to result in a concentration of about 800 mg and about 1000 mg per 250 cubic centimeters in said hard candy object.

12. The method of claim 8, wherein said dispersing step includes dispersing a quantity of tetracaine so as to result in a concentration of between about 1100 mg and about 1500 mg per 250 cubic centimeters in said hard candy object.

13. A method for topically administering tetracaine orally to the buccal mucosa of a patient, the method comprising the steps of:
    inserting into the patient's mouth a hard candy object comprising a quantity of tetracaine dispersed in a hard candy matrix, wherein said quantity of tetracaine is sufficient to provide an effective dose of tetracaine for localized topical administration of tetracaine to said mucosa when said matrix dissolves in the patient's mouth; and
    removing said hard candy object from the patient's mouth after a period of time sufficient for at least a portion of said hard candy object to dissolve in the patient's saliva and provide said effective dose to the patient to achieve a desired local effect of tetracaine on the patient's mucosa;
    wherein said period of time is no greater than about 2 minutes.

14. The method of claim 13, wherein said effective dose provides pain relief without totally anesthetizing said mucosa.

15. The method of claim 13, wherein:
    said hard candy object includes a handle for inserting said object into the patient's mouth, positioning said object in the patient's mouth, and removing said object from the patient's mouth; and
    said method further comprises the step of using said handle to position said hard candy object in the patient's mouth adjacent a selected portion of the patient's mucosa to deliver said effective dose to said selected portion.

16. The method of claim 13, wherein said period of time is between about 30 seconds and about 2 minutes.

17. The method of claim 13, wherein said quantity of tetracaine is between about 700 mg and about 1500 mg per 250 cubic centimeters of said hard candy object.

18. The method of claim 13, wherein said quantity of tetracaine is between about 800 mg and about 1000 mg per 250 cubic centimeters of said hard candy object.

19. The method of claim 13, wherein said quantity of said tetracaine is between about 1100 mg and about 1500 mg per 250 cubic centimeters of said hard candy object.

* * * * *